United States Patent [19]
Murakami et al.

[11] Patent Number: 5,268,213
[45] Date of Patent: Dec. 7, 1993

[54] LIQUID-PERMEABLE TOPSHEET FOR BODY FLUID ABSORBENT ARTICLES

[75] Inventors: Masaki Murakami, Kawanoe; Hiroyuki Inagaki; Yozo Yamada, both of Kakegawa, all of Japan

[73] Assignee: Uni-Charm Corporation

[21] Appl. No.: 416

[22] Filed: Jan. 4, 1993

[30] Foreign Application Priority Data

Jan. 20, 1992 [JP] Japan .................. 4-1540

[51] Int. Cl.$^5$ .................. A61F 13/15; B32B 3/26; B32B 3/30
[52] U.S. Cl. .................. 428/163; 604/385.1
[58] Field of Search .................. 428/163

[56] References Cited

U.S. PATENT DOCUMENTS

| | | |
|---|---|---|
| 2,896,618 | 7/1959 | Schaefer . |
| 3,292,619 | 12/1966 | Egler .................. 428/163 |
| 3,459,618 | 8/1969 | Egler .................. 156/219 |
| 3,877,140 | 4/1975 | Topolsek . |
| 5,114,776 | 5/1992 | Cesaroni .................. 428/131 |

FOREIGN PATENT DOCUMENTS

| | | |
|---|---|---|
| 0018020 | 10/1980 | European Pat. Off. . |
| 0039974 | 11/1981 | European Pat. Off. . |
| 0305123 | 3/1989 | European Pat. Off. . |
| 0313766 | 5/1989 | European Pat. Off. . |
| 2235878 | 3/1991 | United Kingdom . |

OTHER PUBLICATIONS

WO90/11746 (PCT/GB90/00486), Howarth, Oct. 18, 1990.

Primary Examiner—James C. Cannon
Attorney, Agent, or Firm—Fred Philpitt

[57] ABSTRACT

To control a flow of body fluid generally occurring on the liquid-permeable topsheet for body fluid absorbent article in a predetermined direction, here is disclosed an improved liquid-permeable topsheet made of thermoplastic synthetic resin comprising a plurality of first direction ribs and a plurality of second direction ribs crossing the first direction ribs so as to a unique rib-structure. Tops 7 of the second direction ribs 3 are connected with opposite sides 6 of the respective first direction ribs 2 and each pair of adjacent first direction ribs 2 define a groove 10 serving to guide the body fluid in the predetermined direction.

1 Claim, 3 Drawing Sheets

LIQUID-PERMEABLE TOPSHEET FOR BODY FLUID ABSORBENT ARTICLES

BACKGROUND OF THE INVENTION

This invention relates to a liquid-permeable topsheet made of thermoplastic resin used for body fluid absorbent articles such as disposable diapers and sanitary napkins.

Conventionally, nonwoven fabric, perforated thermoplastic sheet or the like has been used as a liquid-permeable topsheet covering an absorbent core of body fluid absorbent articles.

Obviously it is desired that body fluid absorbency of such articles should be as rapid as possible and this will be effectively achieved, for example, by orienting flow of the body fluid on a topsheet or by controlling a diffusion of the body fluid in a predetermined direction so that the body fluid may rapidly spread over the entire surface of the absorbent core. While a topsheet made of nonwoven fabric is preferable in that a certain degree of diffusion can be expected under a capillary effect occurring between component fibres of the nonwoven fabric and the body fluid, it is difficult to realize rapid and direction-controlled diffusion of the body fluid since density of the nonwoven fabric for such application is limited by a requirement that a touch of the topsheet should be soft for user's skin. When the perforated sheet is employed as the topsheet, on the other hand, the body fluid smoothly flows on the sheet surface but can not be direction-controlled.

Accordingly, it is an object of the invention to provide a liquid-permeable topsheet made of thermoplastic resin so improved that a unique rib structure thereof allows a flow of body fluid to be controlled in a predetermined direction.

SUMMARY OF THE INVENTION

The object set forth above is achieved, according to the invention, by a liquid-permeable topsheet made of thermoplastic resin for body fluid absorbent articles, said liquid-permeable topsheet comprising a plurality of first direction ribs each comprising a top longitudinally extending in a first direction and opposite sides curved down-ward from said top and longitudinally extending also in the first direction, and a plurality of second direction ribs each having a top longitudinally extending in a second direction, these first and second direction ribs crossing one another. Each pair of adjacent first direction ribs and each pair of adjacent second direction ribs crossing said pair of adjacent first direction ribs define each liquid-permeable opening. At respective crossings of these first and second direction ribs, the tops of the second direction ribs are connected with the sides of the first direction ribs so as to form a crossed rib structure which is the most important feature of the invention.

With the topsheet having such rib structure, a plurality of first direction ribs extend in parallel to one another in the first direction and each pair of adjacent first direction ribs are held by the second direction ribs to be spaced from each other by a given distance. The top of the second direction ribs are connected to the sides of the first direction ribs and thereby each pair of adjacent first direction ribs define a groove extending in the first direction and having at its bottom the second direction ribs and the openings. The groove facilitates the body fluid to flow in the first direction rather than in the direction which is transverse thereto.

BRIEF DESCRIPTION OF THE DRAWINGS

The invention will be described more in detail with reference to the attached drawings, in which.

PREFERRED EMBODIMENTS OF THE INVENTION

Figure 1:
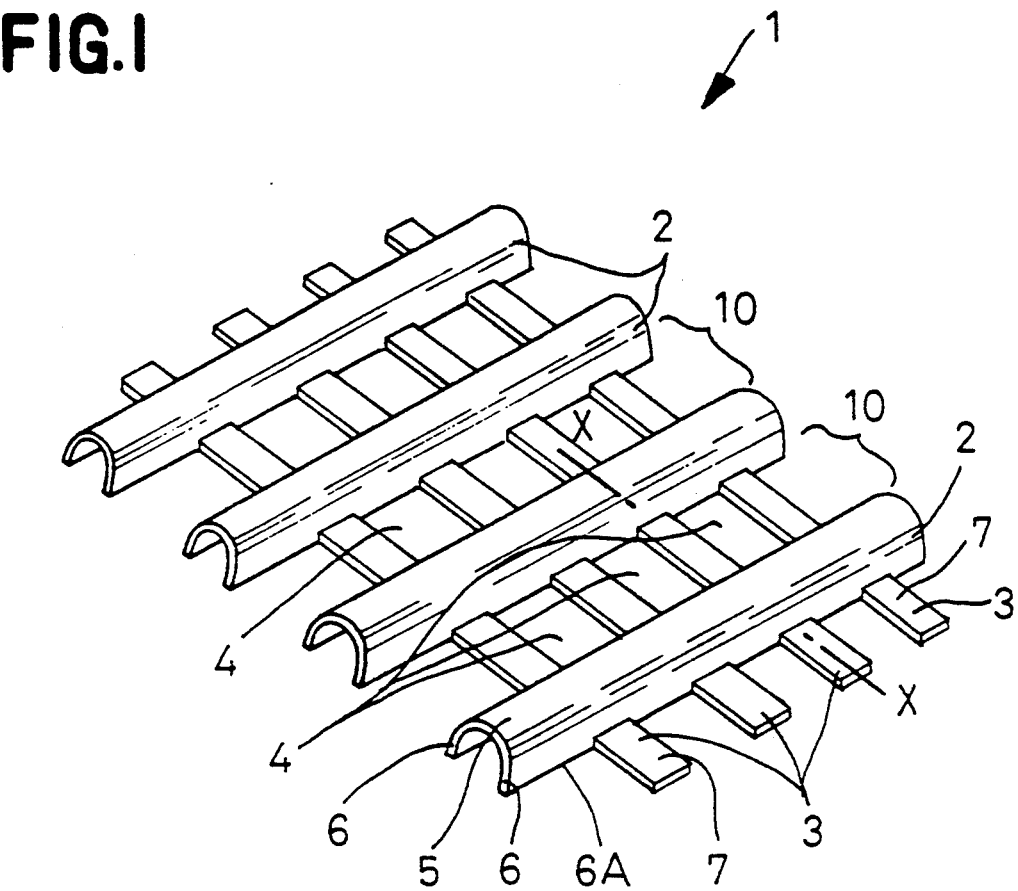
FIG. 1 is a perspective view of the topsheet constructed in accordance with the invention.

FIG. 1 is a perspective view showing a surface configuration of a topsheet 1 constructed according to the invention. The topsheet 1 comprising a plurality of first direction ribs 2 and a plurality of second direction ribs 3 crossing the first direction ribs 2 wherein each pair of adjacent first direction ribs 2 and each pair of adjacent second direction ribs 3 define a liquid-permeable opening 4. Each first direction rib 2 has a top 5 longitudinally extending in the first direction and opposite sides 6 curved downward from said top 5 to respective lower edges 6A. Each second direction rib 3 is flat and sheet-like one longitudinally extending in the second direction and having a top 7 defined by its upper surface. The second direction ribs 3 are connected with the sides 6 of the first direction ribs 2 along their lower edges 6A or adjacent thereto, at respective crossings of the first direction ribs 2 and the second direction ribs 3, and thereby each pair of adjacent first direction ribs 2 are held to be spaced from each other by a predetermined distance so as to form a groove 10 extending in the first direction. This groove 10 comprises at its bottom the second direction ribs 3 and the openings 4 which are liquid-permeable.

Figure 2:
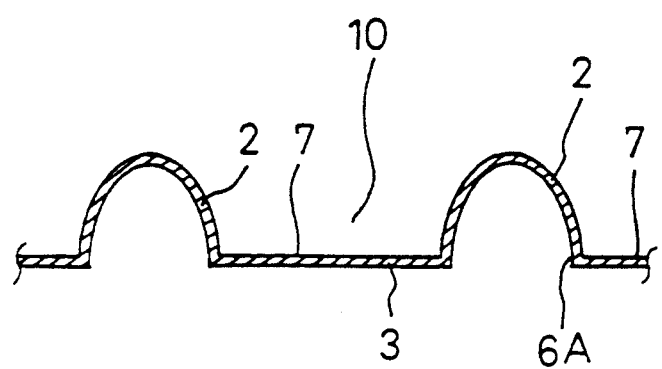
FIG. 2 is a sectional view taken along a line X—X in FIG. 1.

FIG. 2 is a sectional view taken along a line X—X in FIG. 1, showing how the lower edges 6A of the respective first direction ribs 2 are connected with the tops 7 of the respective second direction ribs 3 and how the groove 10 is formed by each pair of adjacent first direction rib 2.

Figure 3:
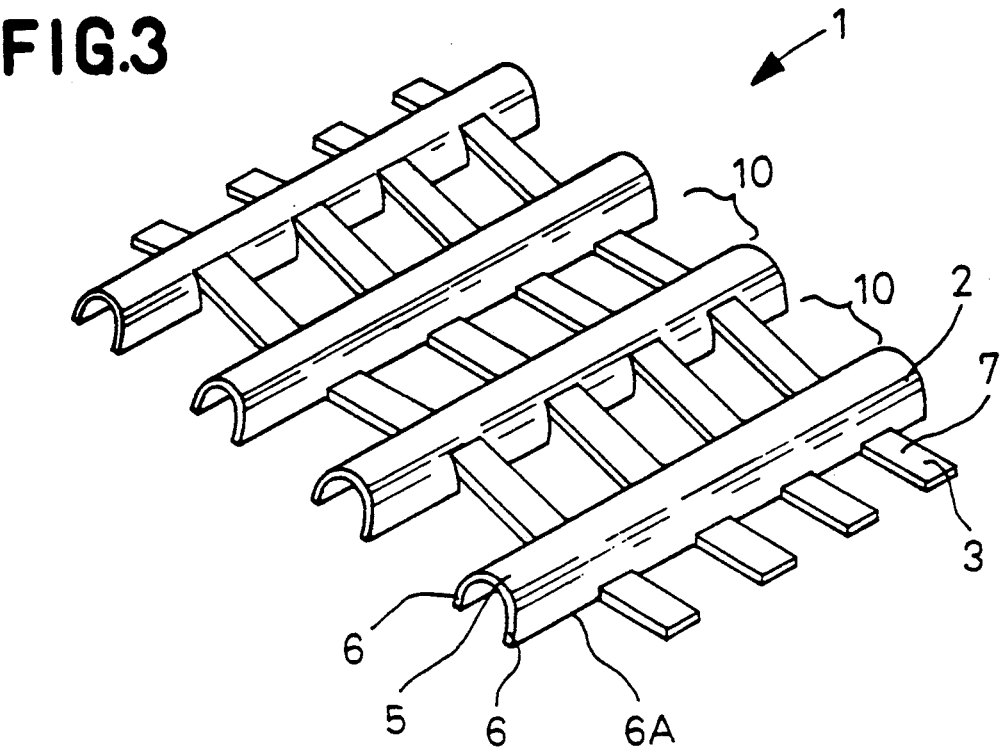
FIG. 3 is a view similar to FIG. 1 but showing another embodiment of the invention.

FIG. 3 is a perspective view similar to FIG. 1 but showing another embodiment of the invention in which the tops 7 of the respective second direction ribs 3 are connected with one of a pair of adjacent first direction ribs 2 adjacent the lower edge 6A of this first direction rib 2 but with the other of the pair of adjacent first direction ribs 2 at upper portion of its side 6. Also in this arrangement, the groove 10 is formed.

Figure 4:
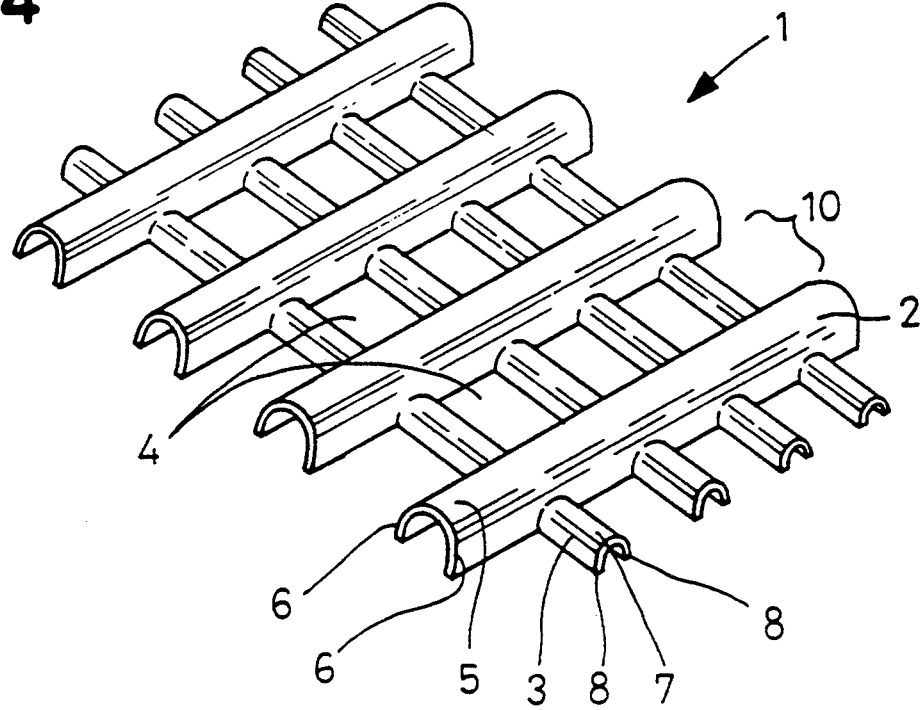
FIG. 4 is a view similar to FIG. 1 but showing still another embodiment of the invention.

FIG. 4 is a perspective view similar to FIG. 1 but showing still another embodiment of the invention, in which the second direction ribs 3 are smaller than the first direction ribs 2 both in width and height but have the tops 7 and the opposite sides 8 which are similar to those of the first direction ribs 2. The tops 7 are connected with the opposite sides 6 of the first direction ribs 2. The tops 7 of the second direction ribs 3 do not project above the tops 5 of the first direction ribs 2 and each pair of adjacent first direction ribs 2 define the groove 10 extending in the first direction.

The respective components of the topsheet 1 are preferred to have dimensions so that the groove 10 has a width of 0.1 to 3 mm as measured between the opposite lower edges 6A of each pair of adjacent first direction ribs 2, the first and second direction ribs 2, 3 have widths of 0.3 to 3 mm, the first direction ribs 2 has a height of 0.2 to 3 mm, the second direction rib 3 has a height smaller than that of the first direction rib 2 and the opening 4 has an area of 0.1 to 9 mm$^2$. The first direction rib 2 has a thickness of 0.02 to 0.2 mm and the second direction rib 3 has a thickness which is equal to or less than the thickness of the first direction rib 2. This topsheet 1 can be obtained by thermoforming suitable thermoplastic sheet such as polyethylene sheet. If the topsheet 1 is hydrophobic, the surface of the topsheet 1 may be subjected to a suitable treatment with a hydrophilic agent to control its wettability with body fluid so that the body fluid may rapidly spread in the first direction under a capillary effect occurring between the side walls of the respective grooves 10 and the body fluid.

Figure 5:
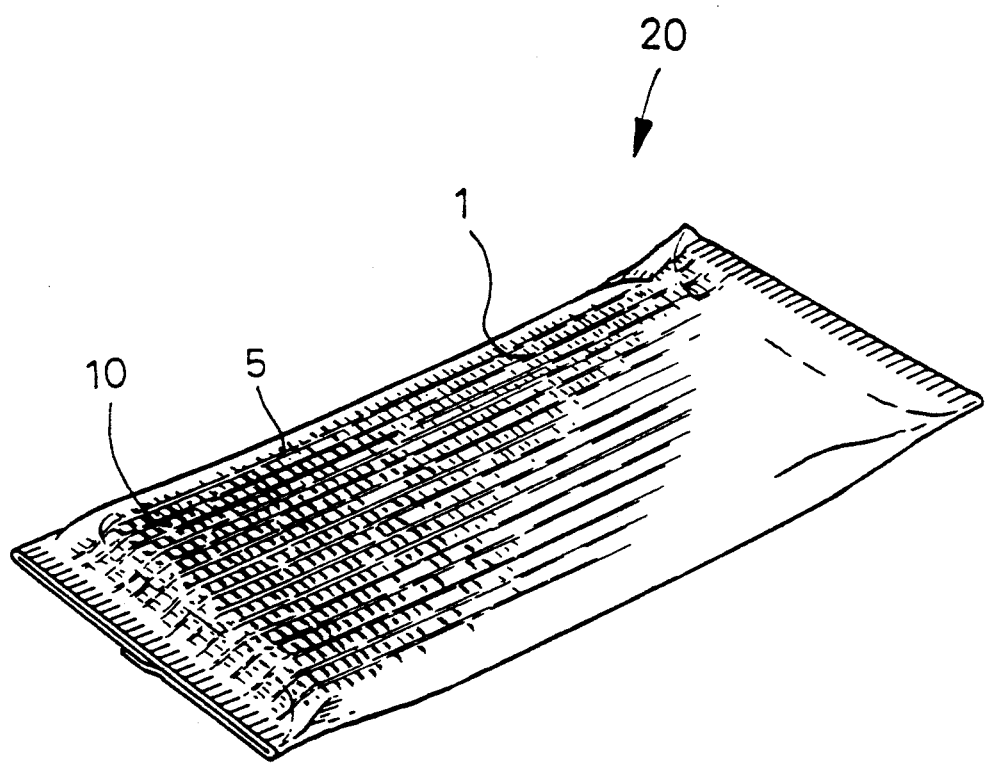
FIG. 5 is a perspective view of sanitary napkin.

FIG. 5 is a perspective view of sanitary napkin 20 employing the topsheet 1 of the invention. The sanitary napkin 20 is tailored in rectangular shape which extend longitudinary in coincidence with the direction of the groove 10. In use of the sanitary napkin, the tops 5 of the respective first direction ribs 2 come in contact with user's skin. Consequently, the body fluid once discharged onto the topsheet 1 rapidly flows along the respective grooves 10 and spreads to the longitudinally opposite ends thereof. A quantity of body fluid flowing transversely of the sanitary napkin is correspondingly suppressed and leak of body fluid can be effectively avoided on both sides of the napkin 20.

The topsheet of the invention allows the flow of body fluid to be controlled by using the topsheet with the grooves being oriented in a predetermined direction and at the same time allows the body fluid leak to be prevented from occurring transversely of the grooves.

What is claimed is:

1. A liquid-permeable topsheet made of thermoplastic resin for body fluid absorbent articles, said liquid-permeable topsheet comprising:

a plurality of first direction ribs each comprising a top longitudinally extending in a first direction and opposite sides curved downward from said top and longitudinally extending also in the first direction and a plurality of second direction ribs each having a top longitudinally extending in a second direction, these first and second direction ribs crossing one another;

each pair of adjacent first direction ribs and each pair of adjacent second direction ribs crossing said pair of adjacent first direction ribs defining each liquid-permeable opening; and at respective crossings of these first and second direction ribs, the tops of the second direction ribs being connected with the sides of the first direction ribs so as to form a crossed rib structure.

* * * * *